(12) United States Patent
Seibel et al.

(10) Patent No.: US 7,583,872 B2
(45) Date of Patent: Sep. 1, 2009

(54) COMPACT SCANNING FIBER DEVICE (75) Inventors: Eric J. Seibel, Seattle, WA (US); Quinn Y. J. Smithwick, Cambridge, MA (US); John A. Myers, Seattle, WA (US); Richard S. Johnston, Sammamish, WA (US); Charles David Melville, Issaquah, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 11/784,488

(22) Filed: Apr. 5, 2007

(65) Prior Publication Data
US 2008/0249369 A1 Oct. 9, 2008

(51) Int. Cl.
G02B 6/26 (2006.01)
(52) U.S. Cl. .................................................. 385/25
(58) Field of Classification Search .................. 385/25, 385/902
See application file for complete search history.

(56) References Cited

U.S. PATENT DOCUMENTS

| | | | |
|---|---|---|---|
| 3,470,320 A | 9/1969 | Pike et al. | |
| 3,644,725 A | 2/1972 | Lochridge, Jr. | |
| 4,206,495 A | 6/1980 | McCaslin | |
| 4,234,788 A * | 11/1980 | Palmer et al. | 250/227.26 |
| 4,264,208 A | 4/1981 | Haberl et al. | |
| 4,710,619 A | 12/1987 | Haberl | |
| 4,743,283 A | 5/1988 | Borsuk | |
| 4,768,513 A | 9/1988 | Suzuki | |
| 4,770,185 A | 9/1988 | Silverstein et al. | |
| 4,782,228 A | 11/1988 | Westell | |
| 4,821,117 A | 4/1989 | Sekiguchi et al. | |
| 4,831,370 A | 5/1989 | Smoot | |
| 4,872,458 A | 10/1989 | Kanehira et al. | |
| 4,963,018 A | 10/1990 | West | |
| 5,081,350 A | 1/1992 | Iwasaki et al. | |
| 5,172,685 A | 12/1992 | Nudelman | |

(Continued)

FOREIGN PATENT DOCUMENTS

EP 1077360 2/2001

(Continued)

OTHER PUBLICATIONS

Barhoum, Erek S., et al., "Optical modeling of an ultrathin scanning fiber endoscope, a preliminary study of confocal versus non-confocal detection", *Optics Express*, vol. 13, No. 19, (Sep. 8, 2005), pp. 7548-7562.

(Continued)

*Primary Examiner*—Charlie Peng
(74) *Attorney, Agent, or Firm*—Blakely Sokoloff Taylor & Zafman LLP (57) ABSTRACT

Scanning fiber devices are disclosed. In one aspect, a scanning fiber device may include an actuator tube. The scanning fiber device may also include a cantilevered free end portion of an optical fiber. The cantilevered free end portion of the optical fiber may have an attached end that is coupled with the actuator tube. The cantilevered free end portion of the optical fiber may also have a free end to be moved by the actuator tube. At least a portion of a length of the cantilevered free end portion of the optical fiber may be disposed within the actuator tube. Methods of using scanning fiber devices are also disclosed.

29 Claims, 6 Drawing Sheets

U.S. PATENT DOCUMENTS

| | | | |
|---|---|---|---|
| 5,178,130 A | 1/1993 | Kaiya |
| 5,315,383 A | 5/1994 | Yabe et al. |
| 5,360,968 A | 11/1994 | Scott |
| 5,454,807 A | 10/1995 | Lennox et al. |
| 5,455,669 A | 10/1995 | Wetteborn |
| 5,459,570 A | 10/1995 | Swanson et al. |
| 5,557,444 A | 9/1996 | Melville et al. |
| 5,596,339 A | 1/1997 | Furness, III et al. |
| 5,627,922 A | 5/1997 | Koelman et al. |
| 5,694,237 A | 12/1997 | Melville |
| 5,695,491 A | 12/1997 | Silverstein |
| 5,701,132 A | 12/1997 | Kollin et al. |
| 5,751,465 A | 5/1998 | Melville et al. |
| 5,784,098 A | 7/1998 | Shoji et al. |
| 5,822,073 A | 10/1998 | Yee et al. |
| 5,822,486 A | 10/1998 | Svetkoff et al. |
| 5,894,122 A | 4/1999 | Tomita |
| 5,903,397 A | 5/1999 | Melville et al. |
| 5,913,591 A | 6/1999 | Melville |
| 5,939,709 A | 8/1999 | Ghislain et al. |
| 5,969,871 A | 10/1999 | Tidwell et al. |
| 5,982,528 A | 11/1999 | Melville |
| 5,982,555 A | 11/1999 | Melville et al. |
| 5,991,048 A | 11/1999 | Karlson et al. |
| 5,995,264 A | 11/1999 | Melville |
| 6,046,720 A | 4/2000 | Melville et al. |
| 6,049,407 A | 4/2000 | Melville |
| 6,061,163 A | 5/2000 | Melville |
| 6,069,698 A | 5/2000 | Ozawa et al. |
| 6,069,725 A | 5/2000 | Melville |
| 6,097,353 A | 8/2000 | Melville et al. |
| 6,154,321 A | 11/2000 | Melville et al. |
| 6,157,352 A | 12/2000 | Kollin et al. |
| 6,166,841 A | 12/2000 | Melville |
| 6,191,761 B1 | 2/2001 | Melville et al. |
| 6,204,832 B1 | 3/2001 | Melville et al. |
| 6,220,711 B1 | 4/2001 | Melville et al. |
| 6,243,186 B1 | 6/2001 | Melville et al. |
| 6,257,727 B1 | 7/2001 | Melville |
| 6,263,234 B1 | 7/2001 | Engelhardt et al. |
| 6,281,862 B1 | 8/2001 | Tidwell et al. |
| 6,285,505 B1 | 9/2001 | Melville et al. |
| 6,288,816 B1 | 9/2001 | Melville et al. |
| 6,291,819 B1 | 9/2001 | Hartley |
| 6,294,775 B1 | 9/2001 | Seibel et al. |
| 6,317,548 B1 | 11/2001 | Rockwell et al. |
| 6,369,953 B2 | 4/2002 | Melville et al. |
| 6,388,641 B2 | 5/2002 | Tidwell et al. |
| 6,411,838 B1 | 6/2002 | Nordstrom et al. |
| 6,441,359 B1 | 8/2002 | Cozier et al. |
| 6,492,962 B2 | 12/2002 | Melville et al. |
| 6,535,183 B2 | 3/2003 | Melville et al. |
| 6,538,625 B2 | 3/2003 | Tidwell et al. |
| 6,560,028 B2 | 5/2003 | Melville et al. |
| 6,563,105 B2 | 5/2003 | Seibel et al. |
| 6,581,445 B1 | 6/2003 | Weiss |
| 6,700,552 B2 | 3/2004 | Kollin et al. |
| 6,734,835 B2 | 5/2004 | Tidwell et al. |
| 6,747,753 B1 | 6/2004 | Yamamoto |
| 6,845,190 B1 | 1/2005 | Smithwick et al. |
| 6,850,673 B2 | 2/2005 | Johnston, II et al. |
| 6,856,712 B2 | 2/2005 | Fauver et al. |
| 6,867,753 B2 | 3/2005 | Chinthammit et al. |
| 6,959,130 B2 | 10/2005 | Fauver et al. |
| 6,975,898 B2 | 12/2005 | Seibel |
| 6,977,631 B2 | 12/2005 | Melville et al. |
| 7,068,878 B2 | 6/2006 | Crossman-Bosworth et al. |
| 7,123,790 B2 * | 10/2006 | Rosman et al. ............... 385/25 |
| 7,159,782 B2 | 1/2007 | Johnston et al. |
| 7,184,150 B2 | 2/2007 | Qualing et al. |
| 7,189,961 B2 | 3/2007 | Johnston et al. |
| 7,230,583 B2 | 6/2007 | Tidwell et al. |
| 7,252,236 B2 | 8/2007 | Johnston et al. |
| 2001/0051761 A1 | 12/2001 | Khadem |
| 2001/0055462 A1 | 12/2001 | Seibel |
| 2002/0062061 A1 | 5/2002 | Kaneko et al. |
| 2002/0064341 A1 | 5/2002 | Fauver et al. |
| 2002/0080359 A1 | 6/2002 | Denk et al. |
| 2002/0093467 A1 | 7/2002 | Tidwell et al. |
| 2002/0093563 A1 | 7/2002 | Cline et al. |
| 2002/0097498 A1 | 7/2002 | Melville et al. |
| 2002/0139920 A1 | 10/2002 | Seibel et al. |
| 2003/0010825 A1 | 1/2003 | Schmidt et al. |
| 2003/0010826 A1 | 1/2003 | Dvorkis et al. |
| 2003/0016187 A1 | 1/2003 | Melville et al. |
| 2003/0048540 A1 | 3/2003 | Xie et al. |
| 2003/0142042 A1 | 7/2003 | Tidwell et al. |
| 2003/0169966 A1 | 9/2003 | Tokizaki |
| 2003/0202361 A1 | 10/2003 | Johnston et al. |
| 2004/0061072 A1 | 4/2004 | Gu et al. |
| 2004/0122328 A1 | 6/2004 | Wang et al. |
| 2004/0153030 A1 | 8/2004 | Novak et al. |
| 2004/0196213 A1 | 10/2004 | Tidwell et al. |
| 2004/0212851 A1 | 10/2004 | Osakabe |
| 2004/0254474 A1 | 12/2004 | Seibel et al. |
| 2005/0020926 A1 | 1/2005 | Wiklof et al. |
| 2005/0025368 A1 | 2/2005 | Glukhovsky |
| 2005/0085708 A1 | 4/2005 | Fauver et al. |
| 2005/0085721 A1 | 4/2005 | Fauver et al. |
| 2005/0174610 A1 | 8/2005 | Fukawa |
| 2005/0182295 A1 | 8/2005 | Soper et al. |
| 2005/0238277 A1 | 10/2005 | Wang et al. |
| 2006/0072189 A1 | 4/2006 | DiMarzio |
| 2006/0072843 A1 | 4/2006 | Johnston |
| 2006/0072874 A1 | 4/2006 | Johnston |
| 2006/0077121 A1 | 4/2006 | Melville et al. |
| 2006/0138238 A1 | 6/2006 | Johnston et al. |
| 2006/0149134 A1 | 7/2006 | Soper et al. |
| 2006/0186325 A1 | 8/2006 | Johnston et al. |
| 2006/0195014 A1 | 8/2006 | Seibel et al. |
| 2006/0226231 A1 | 10/2006 | Johnston et al. |
| 2006/0287647 A1 | 12/2006 | Torchia et al. |
| 2007/0081168 A1 | 4/2007 | Johnston et al. |
| 2007/0091426 A1 | 4/2007 | Johnston et al. |
| 2007/0129601 A1 | 6/2007 | Johnston et al. |
| 2007/0156021 A1 | 7/2007 | Morse et al. |
| 2007/0273930 A1* | 11/2007 | Berier et al. ............... 358/3.26 |

FOREIGN PATENT DOCUMENTS

| | | |
|---|---|---|
| EP | 1360927 | 11/2003 |
| EP | 1864606 | 12/2006 |
| GB | 2057709 | 4/1981 |
| GB | 2378259 | 2/2003 |
| JP | 08-211313 * | 8/1996 |
| WO | WO-9300551 | 1/1993 |
| WO | WO-0174266 | 10/2001 |
| WO | WO-03019661 | 3/2003 |
| WO | WO-2004/040267 | 5/2004 |
| WO | WO-2004040267 | 5/2004 |
| WO | WO-2004068218 | 8/2004 |
| WO | WO-2005009513 | 2/2005 |
| WO | WO-2006004743 | 1/2006 |
| WO | WO-2006041452 | 4/2006 |
| WO | WO-2006041459 | 4/2006 |
| WO | WO-2006071216 | 7/2006 |
| WO | WO-2006096155 | 9/2006 |
| WO | WO-2006/106853 | 10/2006 |
| WO | WO-2006104489 | 10/2006 |
| WO | WO-2006124800 | 11/2006 |
| WO | WO-2007070831 | 6/2007 |

| WO | WO-2008/033168 | 3/2008 |

OTHER PUBLICATIONS

Brown, Christopher, et al., "A Novel Design for a Scanning Fiberoptic Endoscope", *Human Interface Technology Laboratory*, University of Washington, Seattle, WA 98195, Presented at SPIE's Regional Meeting on Optoelectronics, Photonics, and Imaging, (Nov. 1-2, 1999), 1 page.

Brown, Christopher M., et al., "Mechanical Design and Analysis for a Scanning Fiber Endoscope", *Proceedings of 2001 ASME Int'l Mechanical Engineering Congress and Exposition*, BED-vol. 51, (Nov. 11-16, 2001), 165-166.

Chen, Tailian, et al., "Experiment of Coalescence of Dual Bubbles on Micro Heaters", *Department of Mechanical Engineering, University of Florida*, Gainesville, FL 32611-6300. USA., Printed from the Internet Aug. 13, 2006, 1-10.

Fauver, Mark, et al., "Microfabrication of fiber optic scanners", (2002) *In Proceedings of Optical Scanning II, SPIE 4773*, pp. 102-110., 9 pages.

Johnston, Richard S., et al., "Scanning fiber endoscope prototype performance", *Optical Fibers and Sensors for Medical Applications II, Proc. SPIE*, vol. 4616, (Oct. 13, 2004), 173-179.

Seibel, Eric J., et al., "A full-color scanning fiber endoscope", *Optical Fibers and Sensors for Medical Diagnosis and Treatment Applications. Ed I Gannot. Proc. SPIE* vol. 6083, (2006), 9-16.

Seibel, Eric J., et al., "Microfabricated optical fiber with microlens that produces large field-of-view, video rate, optical beam scanning for microendoscopy applications", *Optical Fibers and Sensors for Medical Applications III, Proceedings of SPIE* vol. 4957, (2003), 46-55.

Seibel, Eric J., et al., "Modeling optical fiber dynamics for increased efficiencies in scanning fiber applications", *Optical Fibers and Sensors for Medical Applications V, proceedings of SPIE* vol. 5691, (2005), 42-53.

Seibel, Eric J., et al., "P-37: Optical fiber scanning as a microdisplay source for a wearable low vision aid", *Society for Information Display SID 2002*, Boston, MA, (May 19-24, 2002), 1-4.

Seibel, Eric J., et al., "Prototype scanning fiber endoscope", *Optical Fibers and Sensors for Medical Applications II, Proc. of SPIE*, vol. 4616, (2002), 1-7.

Seibel, Eric J., et al., "Single fiber flexible endocope: general design for small size, high resoljution, and wide field of view", *Human Interface Technology Laboratory, College of Engineering, University of Washington*, Seattle, WA, Proceedings of the SPIE, Biomonitoring and Endoscopy Technologies 4158, (2001), 11 pages.

Seibel, Eric J., et al., "Ultrathin laser scanning bronchoscope and guidance system for the peripheral lung", *11th World Conference on Lung Cancer*, (2005), p. 178.

Seibel, Eric J., et al., "Unique Features of Optical Scanning, Single Fiber Endoscopy", *Lasers in Surgery and Medicine 30*, (2002), 177-183.

Seibel, Eric, et al., "Unique Features of Scanning Fiber Optical Endoscopy", *2000 Annual Fall Meeting Abstracts T4.57*, (2000), 1.

Smithwick, Quinn Y., et al., "54.3: Modeling and Control of the Resonant Fiber Scanner for Laser Scanning Display or Acquisition", *Department of Aeronautics and Astronautics, University of Washington*, Seattle, WA SID 03 Digest, (2003), 1455-1457.

Smithwick, Quinn Y., et al., "A Nonlinear State-Space Model of a Resonating Single Fiber Scanner for Tracking Control: Theory and Experiment", *Transactions fo the ASME*, vol. 126, (Mar. 2004), 88-101.

Smithwick, Quinn Y., et al., "Control Aspects of the Single Fiber Scanning Endoscope", (2001) *SPIE Optical Fibers and Sensors for Medical Applications*, 4253, 176-188., 15 pages.

Smithwick, Quinn Y., et al., "Depth Enhancement using a Scanning Fiber Optical Endoscope", *Department of Aeronautics, Human Interface Technology Laboratory, University of Washington*, Seattle, Washington, Optical Biopsy IV, Proc. SPIE 4613, (2002), 12 pages.

Tuttle, Brandon W., et al., "Delivery of therapeutic laser light using a singlemode silica fiber for a scanning fiber endoscope system", *Optical Fibers and Sensors for Medical Diagnostics and Treatment Applications VI, Proc. of SPIE* Vol. 6083,, (2006), 608307-1 to608307-12.

Wang, Wei-Chih, et al., "Development of an Optical Waveguide Cantilever Scanner", *Opto-Ireland 2002: Optics and Photonics Technologies and Applications, Proceedings of SPIE* vol. 4876 (2003), (2003), 72-83.

Wang, Wei-Chih, et al., "Micromachined opital waveguide cantilever as a resonant optical scanner", *Department of Mechanical Engineering, University of Washington*, Seattle, WA 98195, *Sensors and Actuators A 102*, (2002), 165-175.

"PCT/US2007/009598 International Search Report", (Jan. 3, 2008), 3 pages.

"PCT/US2007/015574 International Search Report", (Mar. 4, 2008), 3 pages.

Brown, Christopher M., et al., "Optomechanical design and fabrication of resonant microscanners for a scanning fiber endoscope", *Optical Engineering*, vol. 45, XP002469237, (Apr. 2006), pp. 1-10.

Smithwick, Y. J., et al., "An error space controller for a resonating fiber scanner: simulation and implementation", *Journal of Dynamic Systems, Measurement and Control*, Fairfiled, N.J., U.S., vol. 128, No. 4, XP009095153, ISSN: 0022-0434, (Dec. 2006), pp. 899-913.

"Non-Final Office Action", U.S. Appl. No. 11/521,523, (Sep. 16, 2008), 1-6.

Smithwick, Y.J., et al., ""An error space controller for a resonating fiber scanner: simulation and implementation"", *Journal of Dynamic Systems, Measurement and Control*, Fairfiled, N.J., U.S., vol. 128, No. 4,, XP009095153, ISSN: 0022-0434 (Dec. 2006), 899-913.

* cited by examiner

COMPACT SCANNING FIBER DEVICE

BACKGROUND

1. Field

Embodiments of the invention relate to scanning fiber devices. In particular, embodiments of the invention relate to scanning fiber devices having at least a portion of a cantilevered free end portion of an optical fiber disposed within an actuator tube, and to methods of making and using such scanning fiber devices.

2. Background Information

Figure 1:
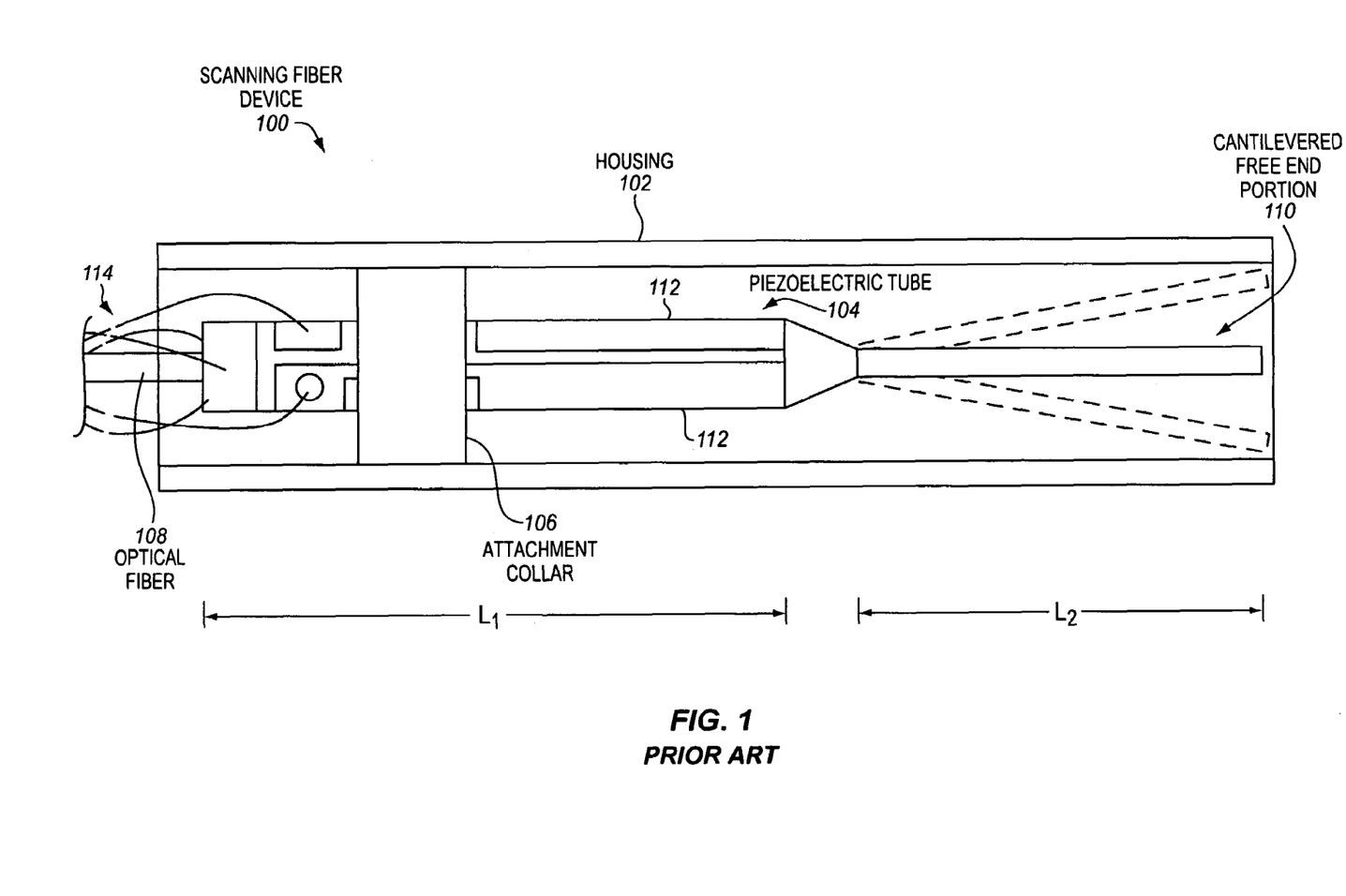
FIG. 1 is a cross-sectional side view of a known scanning fiber device.

FIG. 1 is a cross-sectional side view of a known scanning fiber device 100. The scanning fiber device includes a housing 102. A piezoelectric tube 104 is included in the housing and attached to the housing with an attachment collar 106. A portion of an optical fiber 108 is inserted through the piezoelectric tube. A cantilevered free end portion 110 of the optical fiber is within the housing and attached to a distal end of the piezoelectric tube. The cantilevered free end portion is flexible and may be vibrated or moved. The piezoelectric tube has electrodes 112 thereon. Wires 114 are electrically coupled with the electrodes. The electrodes may be driven to vibrate or otherwise move or scan the cantilevered free end portion of the optical fiber in one or two dimensions.

Dashed lines are used to show that the free end portion of the optical fiber may move. The movement of the optical fiber may be used to acquire an image of an area of interest. For example, the scanning fiber device may scan an illumination spot through an optional lens system and over the area in a scan pattern. Backscattered light may be captured, for example, by one or more optical fibers or photodetectors, in time series.

Notice that in the illustrated scanning fiber device the cantilevered free end portion of the optical fiber is attached to the end of the piezoelectric tube. Attaching the cantilevered free end portion to the end of the piezoelectric tube may have the potential drawback that the length of the housing may need to be longer than desired for certain implementations. In particular, the length of the housing may need to be longer than the sum of the length of the piezoelectric tube (L1) plus the length of the cantilevered free end portion (L2) of the optical fiber. This is due in part to the fact that the lengths of the piezoelectric tube and the cantilevered free end portion of the optical fiber are aligned end-to-end and are substantially non-overlapping.

Generally the housing is relatively rigid in order to provide adequate mechanical protection to the components therein. In the case of certain scanning fiber devices, it may be beneficial to have the option of shortening the length of the rigid housing at the distal end, such as, for example, to facilitate maneuverability and/or insertion of the device into tight confines.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

Figure 2:
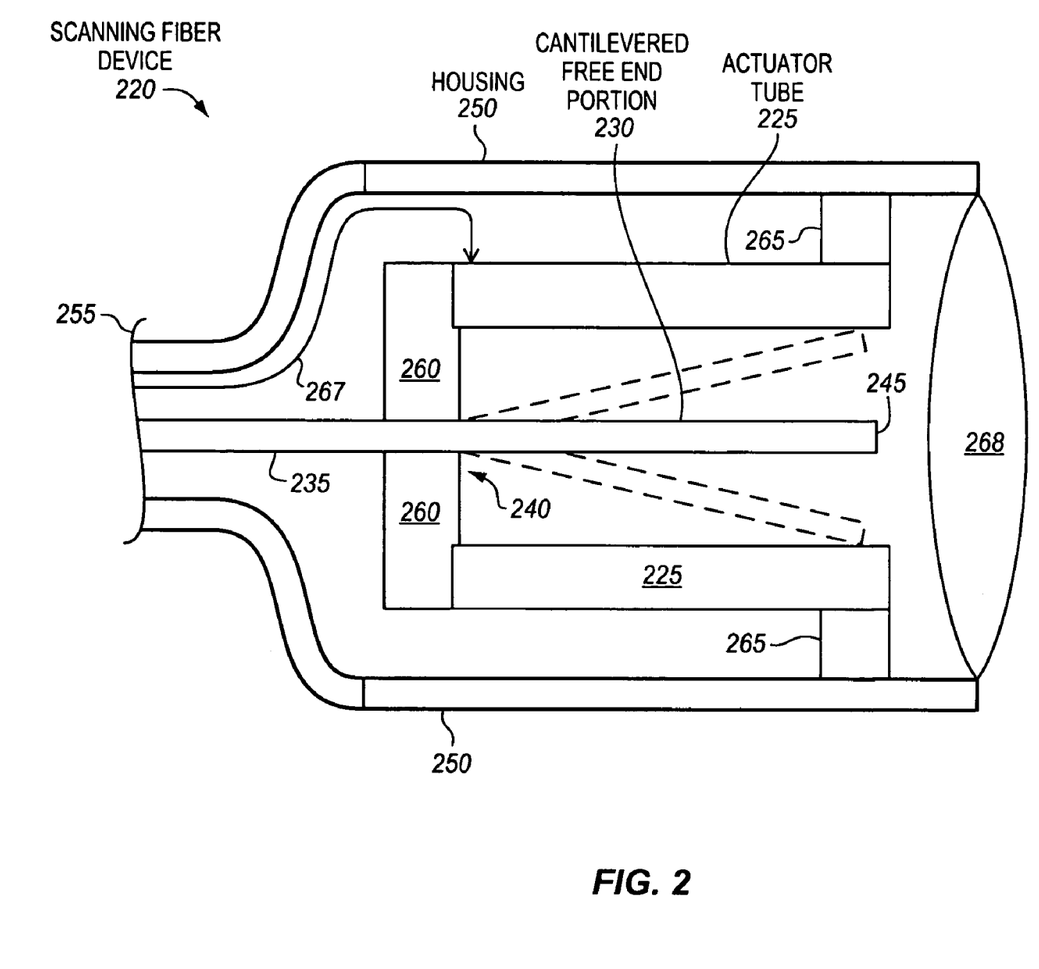
FIG. 2 is a cross-sectional side view of an example scanning fiber device in which substantially all of a cantilevered free end portion of an optical fiber is disposed within an actuator tube, according to embodiments of the invention.

FIG. 2 is a cross-sectional side view of an example scanning fiber device 220, according to embodiments of the invention. The scanning fiber device includes an actuator tube 225, and a cantilevered free end portion 230 of an optical fiber 235. The cantilevered free end portion of the optical fiber has an attached end 240 that is coupled with the actuator tube, and a free end or tip 245 to be moved by the actuator tube. As shown, in embodiments of the invention, at least a portion of a length of the cantilevered free end portion of the optical fiber is disposed within the actuator tube, and may vibrate or move within the actuator tube. As shown in this particular example scanning fiber device, in embodiments of the invention, substantially all of the length of the cantilevered free end portion of the optical fiber may be disposed within the actuator tube, although this is not required.

In various embodiments of the invention, the scanning fiber device may take the form of a scanning fiber endoscope, scanning fiber boroscope, scanning fiber microscope, other type of scanning fiber scope, scanning fiber bar code reader, scanning fiber image display device, or other scanning fiber image acquisition and/or display device known in the art. As is known, an endoscope is an instrument or device to be inserted into a patient that may be used to look inside a body lumen or cavity, or otherwise look inside the patient. The term "endo" is commonly dropped and the body lumen or cavity associated with the "scope" is used to refer to the particular type of instrument. Examples of suitable types of scanning fiber endoscopes include, but are not limited to, bronchoscopes, colonoscopes, gastroscopes, duodenoscopes, sigmoidoscopes, push enteroscopes, choledochoscopes, cystoscopes, hysteroscopes, laryngoscopes, rhinolaryngoscopes, thorascopes, ureteroscopes, arthroscopes, cystoscopes, laparoscope, nephroscopes, otoscopes, sinuscopes, boroscopes, and thorascopes. Endoscopes may also be referred to herein simply as "scopes".

The scanning fiber device also has a housing 250. The housing may represent a material or device of enclosure. As previously mentioned, in some implementations the housing may tend to be relatively rigid, for example, to provide adequate mechanical protection to the components therein. In some implementations, such as, for example, in the case of an endoscope or other device to be inserted into a patient, the housing may be hermetically sealed, although this is not required in other implementations.

Within the housing is the actuator tube 225. The actuator tube is to be interpreted broadly herein as a tube that is capable of actuating or moving the cantilevered free end portion of the optical fiber described below in response to applied signals, commonly electrical. The tube may be a hollow commonly elongated body having at least a portion of the optical fiber therein. Commonly the tube may have a circular cross-section, although elliptical or polygonal cross sections are potentially also suitable. In some embodiments the tube may be cylindrical, although in other embodiments it may be tapered or conical.

In embodiments of the invention, the actuator tube may include a transducer tube. Examples of suitable transducer tubes include, but are not limited to, piezoelectric tubes, electroactive polymer (EAP) tubes, and tubes of other transducing materials that are capable of actuating or moving the cantilevered free end portion of the optical fiber. Another example of a suitable actuator tube is a tube of a material, which need not necessarily be transducing, but which may be actuated by another component, such as, for example, by one or more microelectromechanical systems (MEMS), by another actuating or transducing material or device, or by an applied field. Examples of suitable piezoelectric tubes are commercially available from several sources including, but not limited to: Morgan Technical Ceramics Sales, of Fairfield, N.J.; Sensor Technology Ltd., of Collingwood, Ontario, Canada; and PI (Physik Instrumente) L.P., of Auburn, Mass.

Also within the housing is the cantilevered free end portion 230 of the optical fiber 235. The cantilevered free end portion has the attached, proximal end 240 and the free, distal end or tip 245. The free, distal end or tip of the optical fiber is physically uncoupled and is free to be moved by the actuator tube.

The term "proximal" is used herein to refer to the side of the device or its components that would be closest to an un-illustrated conventional portion 255 of the scanning fiber device (the left-hand side in the illustration). By way of example, in the case of an endoscope, the conventional portion may include a cable and connector to a base station having a light source and drive electronics for the actuator tube. Alternatively, as another example, the light source and the drive electronics and other optional conventional components may be directly integrated within the housing. The term "distal" is used herein to refer to the side of the device or its components that would be closest to a surface of which an image is to be acquired or displayed on (the right-hand side in the illustration).

The attached, proximal end is physically coupled with the actuator tube. As shown, in one or more embodiments, the attached, proximal end may be physically coupled with a proximal end or proximal portion of the actuator tube. The physical coupling may help to fix or firmly secure the attached end with the proximal end or proximal portion of the actuator tube, so that they move together. The attached end provides support for the cantilevered free end portion, which projects horizontally to the right of the attached end, as viewed.

In one or more embodiments, the attached end may optionally be physically coupled with the actuator tube through one or more intervening components 260, although this is not required. For example, a ring-shaped plug may be used to physically couple the attached end with the actuator tube. The ring-shaped plug may have a central hole having the optical fiber inserted therein. An adhesive may optionally be used to adhere the optical fiber in the hole. As another example, a bead of adhesive alone may be used to couple the attached end with the actuator tube. Alternatively, the actuator tube may have a closed end having a hole having the optical fiber inserted therein. If desired, an optional adhesive may be used to adhere the optical fiber in the hole at the closed end of the actuator tube.

As clearly shown, at least a portion of a length of the cantilevered free end portion 230 of the optical fiber is disposed within the actuator tube 225. As shown, in embodiments of the invention, substantially all of the length of the cantilevered free end portion (including its free, distal end or tip) may be disposed within the actuator tube, although this is not required. As used herein, substantially all of the length of the cantilevered free end portion is disposed within the actuator tube when at least 95% of the length of the cantilevered free end portion is disposed within the actuator tube.

In this configuration, the lengths of the actuator tube and the cantilevered free end portion of the optical fiber disposed within the actuator tube overlap or are coextensive. This is in contrast to the configuration of FIG. 1, where substantially all the cantilevered free end portion is outside of the piezoelectric tube, and the lengths of the piezoelectric tube and the entire cantilevered free end portion are aligned end-to-end and are non-overlapping. A potential advantage of disposing at least a portion of the cantilevered free end portion of the optical fiber within the actuator tube is that it is not required that the length of the housing be longer than the sum of the length of the actuator tube plus the length of the cantilevered free end portion. Rather, the length of the housing may optionally and potentially be significantly shorter. In particular the length of the housing may be shortened by a length approaching the length of the cantilevered free end portion of the optical fiber disposed within the actuator tube. As previously mentioned, in the case of certain scanning fiber endoscopes, and certain other scanning fiber devices, it may be beneficial to shorten the length of the housing at the distal end, such as, for example, to facilitate maneuverability and/or insertion of the device into tight confines.

It is to be appreciated that embodiments of the invention are not limited to any particular size and shape of the housing, as this may vary considerably depending upon the particular form assumed by the scanning fiber device. While it is true that in some embodiments the length of the housing may be shortened to take advantage of the fact that at least a portion of the cantilevered free end portion of the optical fiber is disposed within the actuator tube, in other embodiments there may be no need or benefit to shortening the length of the housing. Disposing at least a portion of the cantilevered free end portion of the optical fiber within the actuator tube may offer other potential benefits aside from shortening the length of the housing, such as, for example, better thermal insulation of the cantilevered free end portion, better thermal insulation of an adhesive used to attach the cantilevered free end portion, better mechanical protection of the cantilevered free end portion, or better actuation of the cantilevered free end portion.

Referring again to FIG. 2, the actuator tube is physically coupled with the housing. In one or more embodiments of the invention, the actuator tube may be coupled with the housing with one or more intervening devices or components 265. For example, in embodiments of the invention, an attachment collar may be used to couple the actuator tube with the housing. The attachment collar may include a ring, such as, for example, a metal, ceramic, glass, or plastic ring. Friction, adhesive, soldering, frit glass bonding, or other fasteners known in the arts, may be used to couple the actuator tube to the collar and/or the collar to the housing. As another option, the actuator tube may have a lip or ridge in the place of the attachment collar, and friction, adhesive, soldering, frit glass bonding, or other fasteners known in the arts, may optionally be used to couple the lip or ridge to the housing.

As shown, the actuator tube may be physically coupled with the housing at a distal end or distal portion thereof. The distal end or distal portion of the actuator tube is closest to the free end or tip of the optical fiber, and farthest from the attached end. Coupling the distal end or portion of the actuator tube with the housing may allow the proximal end or portion of the actuator tube, where the attached end is coupled, to have the greatest displacement or movement. This may help to reduce the amount of voltage or energy needed to move or vibrate the cantilevered free end portion of the optical fiber. The scanning fiber device may include one or more wires, traces, or other electrically conductive paths 267 having distal ends that are electrically coupled with the actuator tube to provide electrical signals to the actuator tube to cause the actuator tube to move the cantilevered free end portion of the optical fiber.

Referring again to FIG. 2, the housing includes a transparent portion 268 in an optical path of light directed through the cantilevered free end portion of the optical fiber. Commonly, the transparent portion may include one or more lenses (e.g., a lens system) to help focus light directed through the free distal end or tip, although the scope of the invention is not so limited.

In the case of an image acquisition device, light may be emitted from the free distal end or tip as a beam or illumination spot that may be used to acquire an image of a surface. For such an image acquisition device, in one or more embodiments of the invention, one or more optical fibers (not shown) may be attached around an outside of the housing generally co-aligned with the illustrated optical fiber. The one or more optical fibers may capture light backscattered from the surface and convey the backscattered light to one or more photodetectors in the conventional components 255. Alternatively, one or more photodetectors may be included at the distal end to detect the backscattered light.

Figure 3:
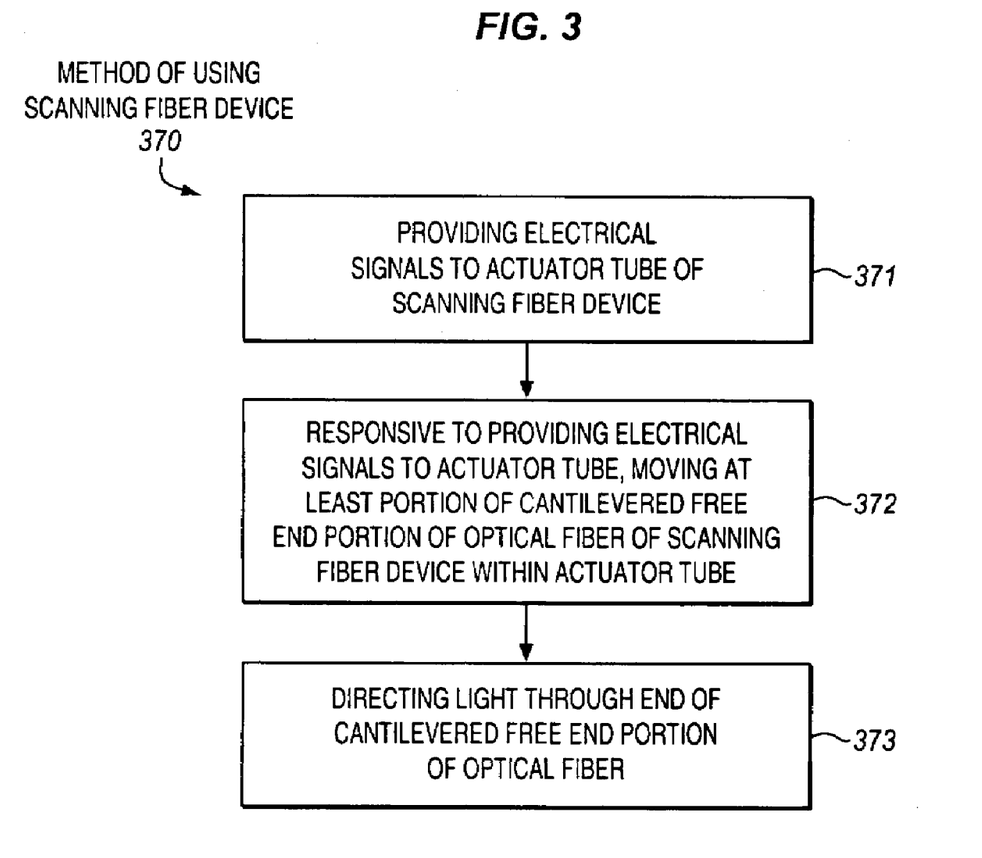
FIG. 3 is a block flow diagram of a method of using a scanning fiber device that includes moving at least a portion of a cantilevered free end portion of an optical fiber within an actuator tube, according to embodiments of the invention.

FIG. 3 is a block flow diagram of a method 370 of using a scanning fiber device, according to embodiments of the invention. At block 371, electrical signals may be provided to the actuator tube of the scanning fiber device, for example through the aforementioned one or more electrically conductive paths.

Responsive to providing the electrical signals to the actuator tube, the actuator tube may actuate or move the cantilevered free end portion. At block 372, at least a portion of the cantilevered free end portion of the optical fiber may vibrate or otherwise move within the actuator tube. By way of example, dashed lines are used in FIG. 2 to show that the cantilevered free end portion of the optical fiber may move within the actuator tube, and to show possible alternate positions of the cantilevered free end portion of the optical fiber as a result of the movement.

Figure 4:
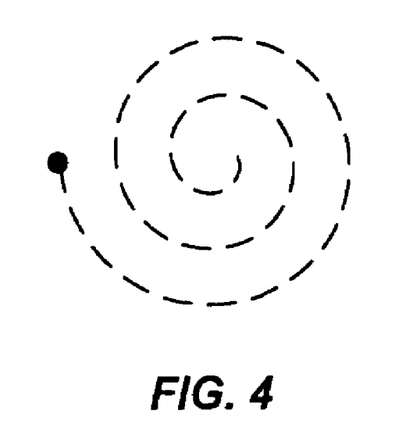
FIG. 4 shows one example of a suitable spiral scan pattern, according to embodiments of the invention.

In embodiments of the invention, the cantilevered free end portion of the optical fiber may be moved in a two-dimensional scan pattern by the actuator tube. Suitable scan patterns include, but are not limited to, radial scan patterns, such as ovals, circles, spirals, propeller patterns, and combinations thereof, and non-radial scan patters, such as raster scan patterns, Lissajous scan patterns, and combinations thereof. FIG. 4 shows one example of a suitable spiral scan pattern, according to embodiments of the invention. The spiral scan pattern may represent the different positions traced by the free, distal tip of the optical fiber throughout the scan and/or in the case of a scanning beam device the positions on a surface of a beam or illumination spot emitted from the end of the free, distal tip throughout the scan. A dot is used to illustrate an instantaneous position in time.

Figure 5:
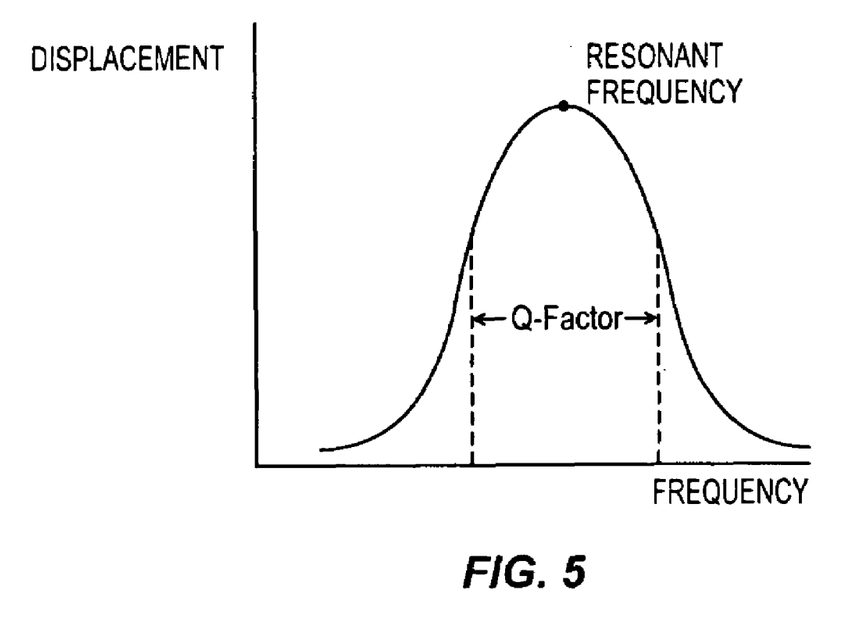
FIG. 5 shows vibrating or moving an optical fiber within a Q-factor of its resonant frequency, according to embodiments of the invention.

While the optical fiber may be vibrated or moved at various frequencies, in embodiments of the invention, the optical fiber may be vibrated or moved close to one of its mechanical or vibratory resonant frequencies (or harmonics thereof), or within a Q-factor of one of its mechanical or vibratory resonant frequencies (or harmonics thereof). FIG. 5 illustrates vibrating or moving an optical fiber within a Q-factor of its resonant frequency to obtain mechanical amplification, according to embodiments of the invention. Frequency is plotted on the x-axis versus displacement on the y-axis. In the illustration, the displacement is shown to have a relatively Gaussian dependency on frequency, with the greatest displacement of the optical fiber occurring at the resonant frequency. In practice, there may be significant deviation from such a Gaussian dependency, although the displacement still typically peaks at the resonant frequency. The ratio of the height of the curve versus the width of the curve is the so-called "Q-factor" of the resonant system. Vibrating or moving the optical fiber within a Q-factor of the resonant frequency may help to reduce the amount of energy needed to perform the scan and/or allow a greater displacement for the same drive signal.

The movement of the optical fiber may be used to construct an image. At block 373, while the cantilevered free end portion of the optical fiber is vibrated or moved during the scan, light may be directed through the free, distal end of the cantilevered free end portion of the optical fiber. Constructing an image may include displaying an image on a surface and/or acquiring an image of a surface. In displaying or forming an image on the surface, the light emitted from the end of the optical fiber may be modulated during the scan depending on the pixel position and passed through a lens system in order to form a desired image on the surface. In acquiring an image of the surface, the scanning fiber device may scan an illumination spot through a lens system and over the surface in the scan. Backscattered light may be captured, for example by a one or more optical fibers or photosensors, in time series.

Referring again to FIG. 2, as shown by the dashed lines, when vibrated in a first mode of resonance, the free, distal end or tip may have the greatest displacement. A certain amount of displacement of the free, distal end or tip may be needed in order to achieve a desired zoom or magnitude of the scan. In order to achieve this desired zoom or magnitude of the scan, the cantilevered free end portion may need to have a certain minimum length. If the configuration of FIG. 1 is used, then the assembled length of the cantilevered free end portion and the actuator tube is generally greater than the sum of each of their individual lengths. However, if the configuration of FIG. 2 is used, then at least some or all of the minimum length of the optical fiber needed to achieve the desired zoom or magnitude of the scan may be vibrated within the actuator tube, and may be coextensive in length with the actuator tube. Advantageously, this latter configuration may allow the same level of zoom or magnitude of the scan (e.g., the same amount of displacement of the free, distal end or tip) to be achieved with a significantly shorter assembled length of the cantilevered free end portion and the actuator tube and/or a significantly shorter housing. Furthermore, the cantilevered free end portion of the optical fiber may alternatively be vibrated in a second mode of resonance, which generally increases the minimum length needed to obtain a desired zoom or magnitude of the scan, and makes the configuration of FIG. 2 even more advantageous.

Now, if substantially all of the cantilevered free end portion of the optical fiber is disposed within the actuator tube and vibrated in a first mode of resonance (where the free, distal end or tip has the greatest displacement), then the inner diameter of the actuator tube may need to be sufficiently large to accommodate the full displacement or swing of the free, distal end or tip, for a desired zoom or magnitude of the scan. However in embodiments of the invention, a distal end portion of the cantilevered free end portion of the optical fiber, which includes the free, distal end or tip, may extend beyond the distal end of the actuator tube.

Figure 6:
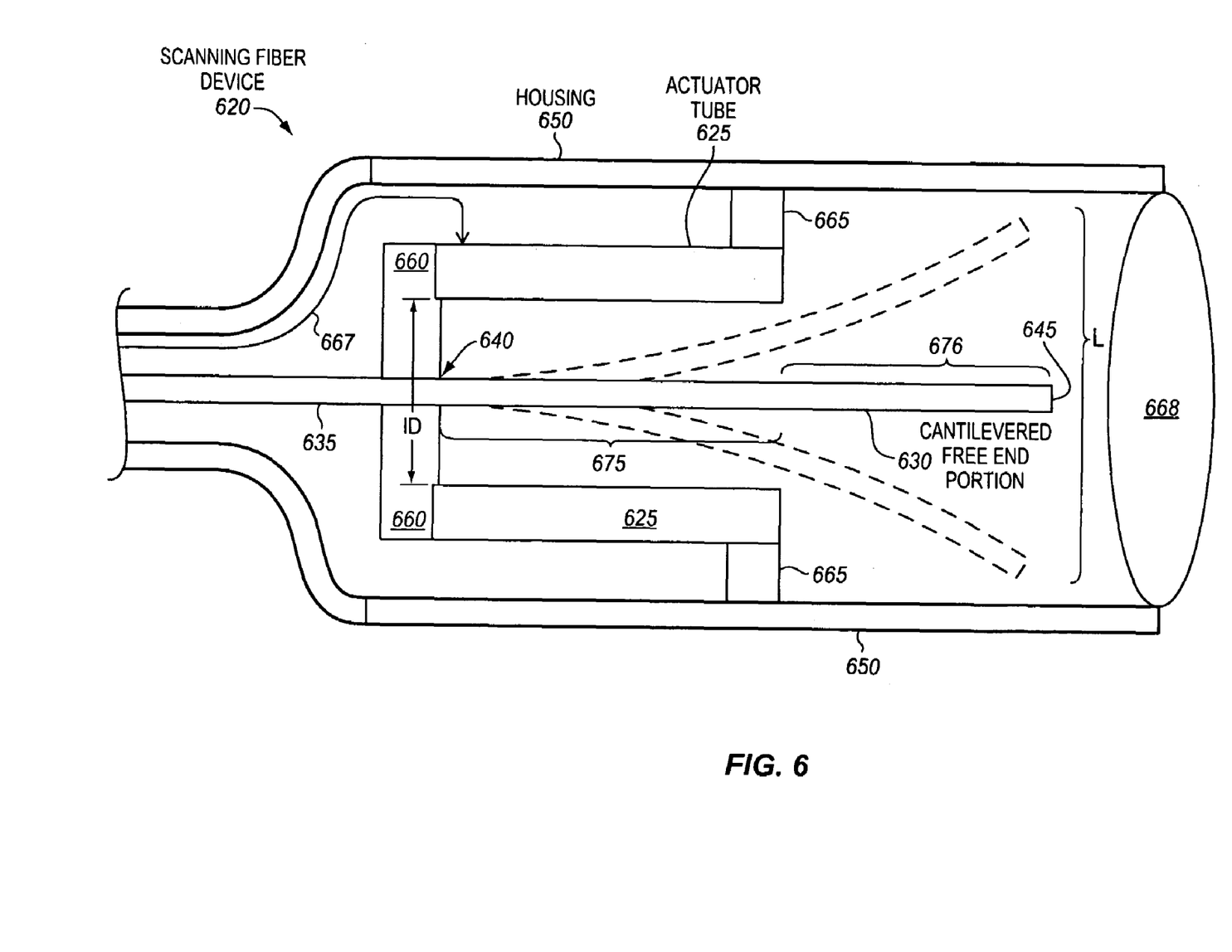
FIG. 6 is a cross-sectional side view of another example scanning fiber device in which a free end of a cantilevered free end portion of an optical fiber extends beyond an end of an actuator tube, according to embodiments of the invention.

FIG. 6 is a cross-sectional side view of another example scanning fiber device 620 in which a free distal end portion 676 of a cantilevered free end portion 630 of an optical fiber 635 extends beyond an end of an actuator tube 625, according to embodiments of the invention. The scanning fiber device includes a housing 650, the actuator tube 625, the cantilevered free end portion 630 of the optical fiber 635, a ring-shaped plug or other physical coupling device or component 660, an attachment collar or other physical coupling device or component 665, one or more electrically conductive paths 667, and a transparent portion of the housing 668. The cantilevered free end portion of the optical fiber has an attached end 640 and a free distal end or tip 645. Unless otherwise specified, these components may optionally have some or all of the characteristics of the corresponding components of the scanning fiber device 220 of FIG. 2. To avoid obscuring certain concepts, the following description will focus primarily on the different and/or additional structures and characteristics of the present example scanning fiber device 620.

As shown, in embodiments of the invention, a proximal portion 675 of a length of the cantilevered free end portion of the optical fiber may be disposed within the actuator tube, and may vibrate or move within the actuator tube. In the illustrated device, slightly more than half of the cantilevered free end portion is disposed within the actuator tube, although this is not required. In alternate embodiments a greater or lesser proportion of the cantilevered free end portion may be disposed with the actuator tube. For example, in various embodiments of the invention, at least a tenth, at least a quarter, or at least half, but not substantially all, of the length of the cantilevered free end portion, may be disposed within the actuator tube. As previously mentioned, disposing at least a portion of the length of the cantilevered free end portion within the actuator tube will help to reduce the overall length of the assembled actuator tube plus cantilevered free end portion.

As further shown, in embodiments of the invention, the distal end portion 676 of the cantilevered free end portion of the optical fiber may extend beyond the distal end of the actuator tube 625. Likewise, the free, distal end or tip 645 may extend beyond the actuator tube.

Extending the distal end portion beyond the actuator tube may optionally and potentially allow the diameter of the actuator tube to be reduced. Dashed lines are used to show possible alternate positions of the cantilevered free end portion of the optical fiber as a result of movement. As shown, the proximal portion may vibrate or move within the actuator tube, whereas the distal end portion, including the free, distal end or tip, may vibrate or move outside of the actuator tube. Notice that in a first mode of resonance the movement of the free, distal end or tip may be displaced or swing through a greater span or length (L) than an inner diameter or other cross-sectional dimension (ID) of the actuator tube. There is no requirement that the inner diameter or cross-sectional dimension of the actuator tube be sufficiently large to accommodate the full swing or displacement of the free, distal end or tip. In this way, allowing the distal end portion to extend beyond the actuator tube may optionally and potentially allow a smaller diameter or cross-section actuator tube to be used, which may help to reduce device dimensions and/or allow a smaller voltage to be used to scan the fiber for a given zoom or magnitude of the scan.

A smaller diameter actuator tube may tend to provide a greater displacement for the same drive voltage than a larger diameter actuator tube, which may tend to simplify the electronics used to drive the actuator tube. However, if at least a portion of the cantilevered free end portion of the optical fiber is to be vibrated or moved within a cylindrical actuator tube, then the diameter or other cross-sectional dimension of the cylindrical actuator tube may need to be large enough to accommodate the vibration or motion of the portion of the cantilevered free end portion of the optical fiber therein. This may result in the diameter or other cross-sectional dimension of the cylindrical actuator tube being larger than desired. In one or more embodiments of the invention, a tapered actuator tube may optionally be used to provide a smaller diameter or cross-sectional dimension at the attached, proximal end to provide greater fiber displacement for the same drive voltage, and a larger diameter or cross-sectional dimension at the free, distal end to provide more space for fiber movement.

Figure 7:
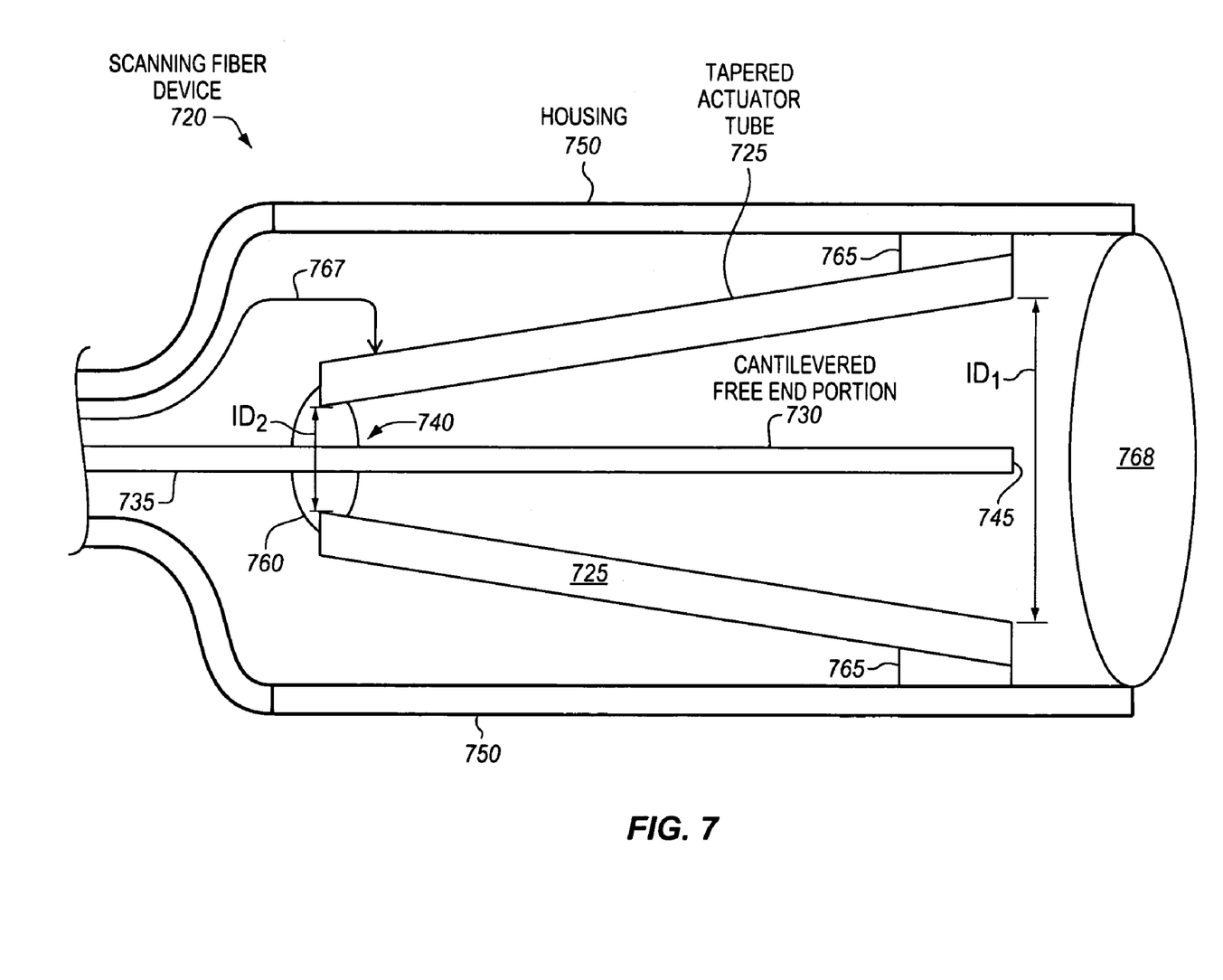
FIG. 7 is a cross-sectional side view of an example scanning fiber device having a tapered actuator tube, according to embodiments of the invention.

FIG. 7 is a cross-sectional side view of an example scanning fiber device 720 having a tapered actuator tube 725, according to embodiments of the invention. The scanning fiber device includes a housing 750, the tapered actuator tube 725, a cantilevered free end portion 730 of an optical fiber 735, a bead of adhesive or other physical coupling device or component 760, an attachment collar or other physical coupling device or component 765, one or more electrically conductive paths 767, and a transparent portion of the housing 768. The cantilevered free end portion of the optical fiber has an attached end 740 and a free distal end or tip 745. Unless otherwise specified, these components may optionally have some or all of the characteristics of the correspondingly named components of the scanning fiber device 220 shown in FIG. 2. To avoid obscuring certain concepts, the following description will focus primarily on the different and/or additional structures and characteristics of the example scanning fiber device 720.

The tapered actuator tube is tapered and becomes progressively smaller in diameter or cross-section toward one end. In particular, as viewed the tapered actuator tube becomes progressively smaller in diameter or cross-section from a right, distal side to a left, proximal side. By way of example, tapered piezoelectric tubes may be made by molding or micromachining.

The tapered actuator tube has a first inner diameter or other cross-sectional dimension (ID1) at a distal end, and a second inner diameter or other inner cross-sectional dimension (ID2) at a proximal end. The first and second inner diameters may be substantially different. As used herein, the first and second diameters may be substantially different if they differ by more than 10%. In particular, the first inner diameter at the distal end, where there is more movement of the cantilevered free end portion of the optical fiber, may be larger than the second inner diameter at the proximal end, where the cantilevered free end portion of the optical fiber is attached.

The first and second inner diameters may differ by different amounts. Typically, the first inner diameter at the distal end may be from about 10% to 1000% larger than the second inner diameter at the proximal end. Commonly, the first inner diameter may be from about 50% to 500% larger than the second inner diameter. In certain embodiments, the first inner diameter may be from about 50% to 300% larger than the second inner diameter. In one particular embodiment, the first inner diameter may be about twice as large as the second inner diameter.

Commonly the tapered actuator tube may have a shape of a truncated hollow cone, although this is not required. Truncated oval-based hollow cones, or truncated polygonal-based pyramids are also potentially suitable.

Another potential advantage of the tapered actuator tube may lie in the physical coupling or attachment of the cantilevered free end portion of the optical fiber. The relatively smaller inner diameter or other cross-sectional dimension of the tapered actuator tube at the proximal end may tend to facilitate physical coupling of the attached end with the actuator tube with an adhesive. The relatively small inner diameter or cross-section may also tend to promote accurate centering of the optical fiber in the actuator tube opening.

In the illustrated example of the scanning fiber device, substantially all the cantilevered free end portion of the optical fiber (including its free, distal end or tip), is disposed within the tapered actuator tube, although this is not required. However, it is to be appreciated that in alternate embodiments, a distal end portion of the cantilevered free end portion of the optical fiber may extend beyond the distal end of the tapered actuator tube as previously described.

In the description and claims, the terms "coupled" and "connected," along with their derivatives, are used. Unless specified otherwise, these terms are not intended as synonyms for each other. Rather, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other physically, electrically, or optically. For example, a cantilevered free end portion of an optical fiber may be coupled with an actuator tube through a ring-shaped plug and/or adhesive, or other intervening devices and/or components.

In the description and claims, unless specified otherwise, the term "scanning" in "scanning fiber device", and the like, does not imply that the device is in use, or presently in the process of scanning, unless otherwise specified. Rather, the term "scanning" merely implies that the device is capable of scanning.

In the description above, for the purposes of explanation, numerous specific details have been set forth in order to provide a thorough understanding of the embodiments of the invention. The particular embodiments described are not provided to limit the invention but to illustrate it. Embodiments may be practiced without some of these specific details. Furthermore, modifications may be made to the embodiments disclosed herein, such as, for example, to the sizes, shapes, configurations, forms, functions, materials, and manner of operation, and assembly and use, of the components of the embodiments. All equivalent relationships to those illustrated in the drawings and described in the specification are encompassed within embodiments of the invention. The scope of the invention is not to be determined by the specific examples provided above but by the claims below. Further, where considered appropriate, terminal portions of reference numerals have been repeated among the FIGURES to indicate corresponding or analogous elements, which may optionally have similar characteristics.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A scanning fiber endoscope comprising:
   a housing of the scanning fiber endoscope, the housing having a length that is less than 20 millimeters and a thickness that is less than 5 millimeters;
   a piezoelectric tube within the housing, a distal end of the piezoelectric tube physically coupled with the housing, wherein the piezoelectric tube is tapered, wherein the tapered piezoelectric tube has a first inner diameter at the distal end and a second inner diameter at a proximal end of the piezoelectric tube, and wherein the first inner diameter is larger than the second inner diameter;
   a cantilevered free end portion of an optical fiber, the cantilevered free end portion having an attached, proximal end that is physically coupled with the proximal end of the piezoelectric tube and a free, distal end to be moved by the piezoelectric tube, wherein at least a quarter of a length of the cantilevered free end portion is disposed within the piezoelectric tube; and
   a transparent material of the housing in an optical path of light directed through the cantilevered free end portion.

2. The scanning fiber endoseope of claim 1, wherein substantially all the length of the cantilevered free end portion is disposed within the piezoelectric tube.

3. The scanning fiber endoscope of claim 1, wherein the free, distal end extends beyond the piezoelectric tube.

4. A scanning fiber device comprising:
   a piezoelectric tube, wherein the piezoelectric tube is tapered, and wherein an inner cross-sectional length at a distal end of the piezoelectric tube is larger than an inner cross-sectional length at a proximal end of the piezoelectric tube;
   a cantilevered free end portion of an optical fiber, the cantilevered free end portion of the optical fiber having an attached end that is coupled with the piezoelectric tube and a free end to be moved by the piezoelectric tube, and wherein at least a portion of a length of the cantilevered free end portion of the optical fiber is disposed within the piezoelectric tube.

5. The scanning fiber device of claim 4, wherein at least a quarter of the length is disposed within the piezoelectric tube.

6. The scanning fiber device of claim 5, wherein substantially all the length of the cantilevered free end portion of the optical fiber is disposed within the piezoelectric tube.

7. The scanning fiber device of claim 4, wherein the free end of the cantilevered free end portion of the optical fiber extends beyond the piezoelectric tube.

8. The scanning fiber device of claim 4, wherein the attached end is physically coupled with a first portion of the piezoeleetric tube that is farthest from the free end of the cantilevered free end portion, and wherein a second portion of the piezoelectric tube that is closest to the free end of the cantilevered free end portion is physically coupled with a housing.

9. The scanning fiber device of claim 4, wherein the inner cross-sectional length at the distal end is from 50% to 500% larger than the inner cross-sectional length at the proximal end.

10. The scanning fiber device of claim 4, further comprising a plug physically coupling the attached end with the piezoelectric tube, wherein the plug has a hole having the optical fiber therein.

11. The scanning fiber device of claim 4, wherein the scanning fiber device comprises an endoscope, and wherein the endoscope further comprises:
 a housing having the piezoelectric tube and the cantilevered free end portion therein, the housing physically coupled with the piezoelectric tube, the housing having a length that is less than 20 millimeters and a thickness that is less than 5 millimeters; and
 a transparent material of the housing in an optical path of light directed through the cantilevered free end portion.

12. A method of using a scanning fiber device comprising:
 providing electrical signals to a piezoelectric tube of the scanning fiber device;
 responsive to providing the electrical signals to the piezoelectric tube, moving at least a portion of a cantilevered free end portion of an optical fiber of the scanning fiber device within the piezoelectric tube, wherein said moving comprises moving the portion of the cantilevered free end portion within a tapered piezoeiectric tube, and wherein the tapered piezoelectric tube has a greatest cross-sectional length closest to a free end of the cantilevered free end portion of the optical fiber; and directing light through the free end of the cantilevered free end portion of the optical fiber.

13. The method of claim 12, wherein moving comprises moving at least one quarter of a length of the cantilevered free end portion within the piezoelectric tube.

14. The method of claim 13, wherein moving comprises moving substantially all the length of the cantilevered free end portion within the piezoelectric tube.

15. The method of claim 12, further comprising moving a free tip of the cantilevered free end portion which extends beyond an end of the piezoelectric tube.

16. The method of claim 12, further comprising swinging a free tip of the cantilevered free end portion of the optical fiber through a greater span than an inner diameter of the piezoelectric tube.

17. The method of claim 12, wherein moving comprises vibrating the cantilevered free end portion of the optical fiber within a Q-factor of its resonance frequency.

18. The method of claim 12, wherein moving comprises vibrating the cantilevered free end portion of the optical fiber in a first mode of resonance.

19. The method of claim 12, wherein moving comprises moving the cantilevered free end portion of the optical fiber in a scan pattern selected from a spiral scan pattern, a propeller scan pattern, a raster scan pattern, and a Lissajous scan pattern.

20. The method of claim 12, further comprising inserting the scanning fiber device into a patient.

21. The scanning fiber endoscope of claim 1, wherein the proximal end of the piezoelectric tube is operable to move in order to move the cantilevered free end portion of the optical fiber.

22. The scanning fiber device of claim 4, wherein a portion of the piezoelectric tube that is coupled with the attached end is operable to move in order to move the cantilevered free end portion of the optical fiber.

23. The scanning fiber device of claim 4, wherein the scanning fiber device comprises a scanning fiber endoscope.

24. A scanning fiber device comprising:
 a housing;
 an actuator tube within the housing, a distal portion of the actuator tube physically coupled with the housing, wherein the actuator tube is tapered;
 a cantilevered free end portion of an optical fiber, the cantilevered free end portion of the optical fiber having an attached, proximal end that is physically coupled with a proximal portion of the actuator tube and a free end to be moved by the actuator tube,
 wherein at least a quarter of a length of the cantilevered free end portion of the optical fiber is disposed within the actuator tube, and
 wherein the proximal portion of the actuator tube is operable to move in order to move the cantilevered free end portion of the optical fiber.

25. The scanning fiber device of claim 24, wherein substantially all the length of the cantilevered free end portion of the optical fiber is disposed within the actuator tube.

26. The scanning fiber device of claim 24, wherein the free end of the cantilevered free end portion of the optical fiber extends beyond the actuator tube.

27. A scanning fiber device comprising:
 a housing;
 a cantilevered actuator tube within the housing and physically coupled with the housing, the cantilevered actuator tube having a distal end and a proximal end, the distal end physically coupled with the housing, the proximal end to be displaced when the cantilevered actuator tube is actuated, wherein the actuator tube is tapered, wherein the tapered actuator tube has a first inner diameter at the distal end and a second inner diameter at the proximal end, and wherein the first inner diameter is larger than the second inner diameter;
 a cantilevered free end portion of an optical fiber, the cantilevered free end portion of the optical fiber having a proximal end that is physically coupled with the proximal end of the actuator tube and a free end.

28. The scanning fiber device of claim 27, wherein at least half of a length of the cantilevered free end portion of the optical fiber is disposed within the actuator tube and is operable to vibrate within the actuator tube.

29. The scanning fiber device of claim 27, wherein the actuator tube comprises a piezoelectric tube, wherein the scanning fiber device comprises an endoscope, and wherein the housing has a length that is less than 20 millimeters and a thickness that is less than 5 millimeters.

* * * * *

UNITED STATES PATENT AND TRADEMARK OFFICE
CERTIFICATE OF CORRECTION

PATENT NO. : 7,583,872 B2
APPLICATION NO. : 11/784488
DATED : September 1, 2009
INVENTOR(S) : J. Seibel et al.

It is certified that error appears in the above-identified patent and that said Letters Patent is hereby corrected as shown below:

In column 10, at line 35 delete, "endoseope" and insert --endoscope--.

Signed and Sealed this
Fourth Day of January, 2011

David J. Kappos
*Director of the United States Patent and Trademark Office*